US00PP09444P

United States Patent [19]

VandenBerg

[11] Patent Number: Plant 9,444

[45] Date of Patent: Jan. 30, 1996

[54] CHRYSANTHEMUM PLANT NAMED 'PINK BLUSH'

[75] Inventor: Cornelis P. VandenBerg, Salinas, Calif.

[73] Assignee: Yoder Brothers Inc., Barberton, Ohio

[21] Appl. No.: 331,863

[22] Filed: Nov. 1, 1994

[51] Int. Cl.[6] ..... A01H 5/00

[52] U.S. Cl. ..... Plt./74.1

[58] Field of Search ..... Plt./74.1, 82.4

[56] References Cited

U.S. PATENT DOCUMENTS

| | | | |
|---|---|---|---|
| P.P. 7,985 | 9/1992 | VandenBerg | Plt./82.4 |
| 4,616,099 | 10/1986 | Sparkes | 47/58 |

OTHER PUBLICATIONS

Broertjes, et al., 1980, "A mutant of a mutant of a . . . Irradiation of progessive radiation induced mutants in a mutation breeding programme with *C. morifolium,*" Euphytica 29:526–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Publ. Co., New York, pp. 162–175.

Scarle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes 1966, "Mutation breeding of Chrysanthemums", Euphytica, 15:156–162.

Dowrick, et al., 1966, "The induction of mutations in Chrysanthemum using X– and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Pink Blush particularly characterized by its flat capitulum form; daisy capitulum type; light pink ray floret color; diameter across face of capitulum of 117 to 133 mm when fully opened, when grown as a pinched disbudded pot mum; photoperiodic flowering response to short days of 49 to 55 days; plant height, with 20 to 22 long days after sticking unrooted cuttings and with 1 to 2 applications of 2500 ppm B-9 SP, ranges from 23 to 28 cm when grown as a pinched pot mum with 4 cuttings in a 15 cm pot; branching pattern is semi-spreading, each plant having 3 to 5 laterals after pinch; and recommended as disbudded pot mum.

1 Drawing Sheet

The present invention comprises a new and distinct cultivar of Chrysanthemum, botanically known as *Dendranthema grandiflora,* and referred to by the cultivar name Pink Blush.

Pink Blush, identified as 5659 (86-627CO2), is a product of a mutation induction program. The new cultivar was discovered and selected by Cornelis P. VandenBerg on Jul. 23, 1990 in a controlled environment in Salinas, Calif., as one flowering plant within a flowering block established as rooted cuttings from stock plants which had been exposed as unrooted cuttings to an X-ray source of 2000 rads in Fort Myers, Fla., on Jan. 25, 1990. The irradiated parent cultivar was the cultivar identified as Blush, disclosed in U.S. Plant Pat. No. 7,985, and described as a disbud daisy pot mum with a flat capitulum form; soft pink ray floret color; diameter across face of capitulum of 114 to 140 mm when fully opened, when grown as a pinched disbudded pot mum; flowering response period of 47 to 55 days after start of short days; plant height of 23 to 28 cm with 1 to 3 applications of 2500 ppm B-9 SP when grown as a pinched pot mum in a 15 cm pot; semi-spreading branching pattern, with 3 to 5 laterals after pinch; and recommended as a disbudded pot mum. The description of Blush has a wider range of measurements than the patented description of Blush, based on the continued flowering trails of Blush after filing the plant patent application for Blush.

The irradiation program resulting in Pink Blush had as its primary objective the expansion of color ranges of the parent cultivar Blush. The irradiation program comprised irradiating cuttings of the parent cultivar at irradiation levels of 1500, 1750 and 2000 rads. A total of 1433 cuttings harvested from a total of 225 irradiated plants were planted on May 28, May 21 and May 14, 1990, respectively. Of these, 19 initial selections were made, which selections were then revegetated and reflowered. Three consecutive flowerings resulted in discarding 12 of the original 19 selections no Apr. 23, 1991. Seven selections were retained and given PI (Possible Introduction) status. Continued flowering trails resulted in discarding 3 of the 7 remaining selections, and the decision to introduce 2 of the remaining selections in North America as White Blush and Coral Blush, disclosed in application Ser. Nos. 08/296,467 and 08/296,466, respectively, and to introduce the other remaining selections in Europe as Orange Blush and Pink Blush, in addition to White Blush and Coral Blush. Orange Blush is disclosed in application Ser. No. 08/331,856.

The first act of asexual reproduction of Pink Blush was accomplished when vegetative cuttings were taken from the initial selection in September 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Pink Blush are firmly fixed and are retained through successive generations of asexual reproduction.

Pink Blush has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Pink Blush, which, in combination, distinguish this chrysanthemum as a new and distinct cultivar:

1. Flat capitulum form.
2. Daisy capitulum type.
3. Light pin ray floret color.
4. Diameter across face of capitulum of 117 to 133 mm when fully opened, when grown as pinched disbudded pot mum.
5. Photoperiodic flowering response to short days of 49 to 55 days.
6. Plant height, with 20 to 22 long days after sticking unrooted cuttings and with 1 to 2 applications of 2500 ppm B-9 SP, ranges from 23 to 28 cm when grown as a pinched pot mum with 4 cuttings in a 15 cm pot.
7. Branching pattern is semi-spreading, each plant having 3 to 5 laterals after pinch.
8. Recommended as disbudded pot mum.

The accompanying photographic drawing is a side view of a potted mum of Pink Blush, with 4 cuttings in a 15 cm pot, with the colors being as nearly true as possible with illustrations of this type.

Of the commercial cultivars known to the inventor, the most similar in comparison to Pink Blush is the parent cultivar Blush. All traits of Pink Blush are similar to those of Blush, except for ray floret color and the diameter of capitulum. The ray floret color of Pink Blush is darker pink (75A to 75B) than the soft pink ray floret color of Blush (75B to 75C). Diameter of capitulum of Pink Blush has been typically smaller by approximately 10 to 11 mm than the diameter of capitulum of Blush, when the cultivars are grown side by side under the same conditions.

In the following description, color references are made to the Royal Horticultural Society Colour Chart. The color values were determined on plant material grown as a pinched disbudded pot mum in Salinas, Calif. on Feb. 25, 1993.

Classification:

*Botanical.*—*Dendranthema grandiflora* cv Pink Blush.
*Commercial.*—Flat daisy disbud pot mum.

INFLORESCENCE

A. Capitulum:
*Form.*—Flat.
*Type.*—Daisy.
*Diameter across face.*—117 to 133 mm when fully opened.

B. Corolla of ray florets:
*Color (general tonality from a distance of three meters).*—Light pink.
*Color (upper surface).*—75A to 75B; in summer when just opening, 75A compared to 75C for ray florets of Blush.
*Color (under surface).*—75C to 75D.
*Shape.*—Straight, pointed, slightly ribbed.

C. Corolla of disc florets:
*Color (mature).*—7B.
*Color (immature).*—144A to 144B.

D. Reproductive organs:
*Androecium.*—Present on disc florets only; scant pollen.
*Gynoecium.*—Present on both ray and disc florets.

PLANT

A. General appearance:
*Height.*—23 to 28 cm when grown as a pinched pot mum with 20 to 22 long days prior to start of short days, and with 1 to 2 applications of 2500 ppm B-9 SP.
*Branching pattern.*—Semi-spreading, with 3 to 5 laterals after pinch.

B. Foliage:
*Color (upper surface).*—147A.
*Color (under surface).*—147B.
*Shape.*—Moderately lobed and slightly serrated.

I claim:

1. A new and distinct Chrysanthemum plant named Pink Blush, as described and illustrated.

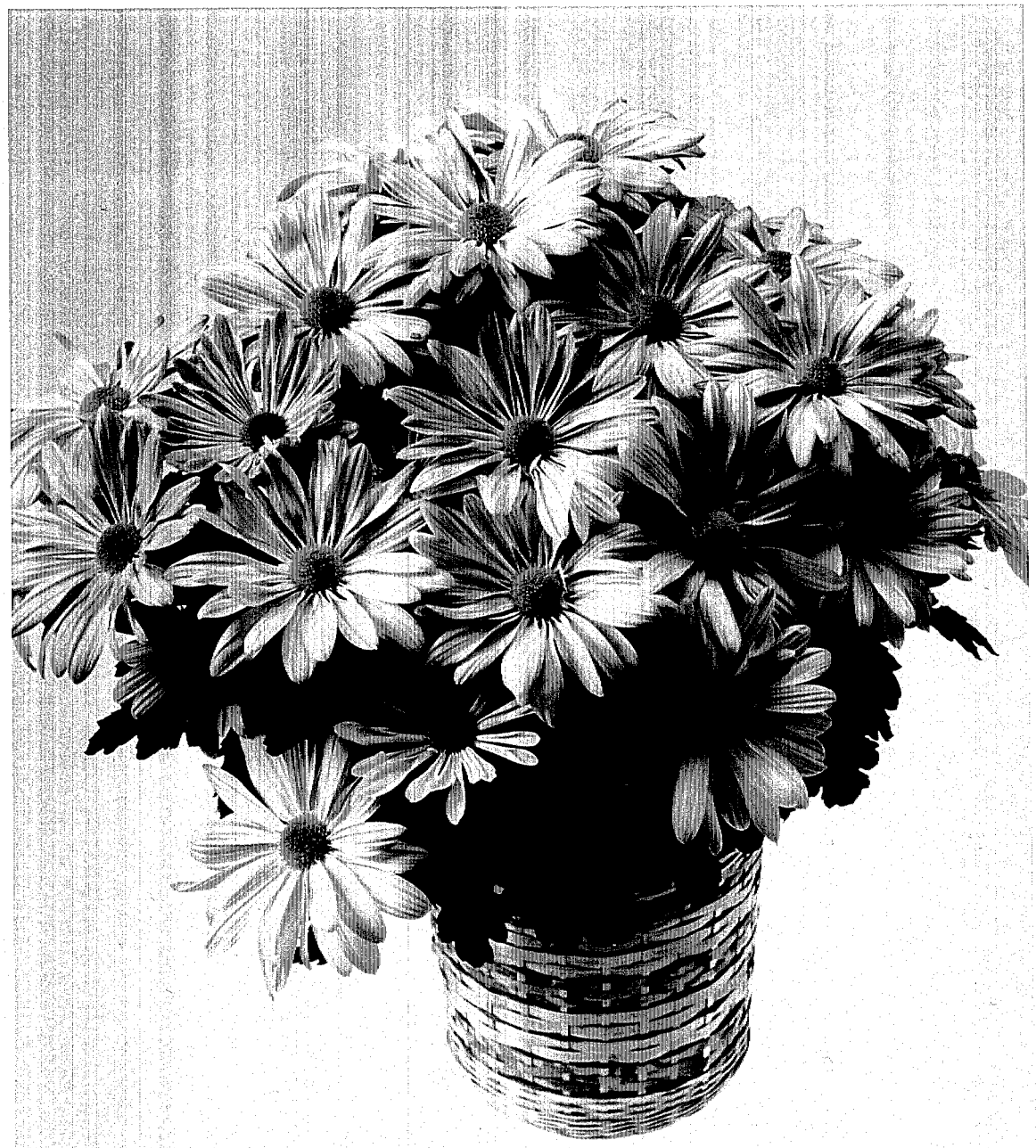

* * * * *